US009588078B2

(12) United States Patent
Adachi et al.

(10) Patent No.: US 9,588,078 B2
(45) Date of Patent: Mar. 7, 2017

(54) GAS SENSOR

(71) Applicant: NGK INSULATORS, LTD., Nagoya-shi, Aichi (JP)

(72) Inventors: Yosuke Adachi, Nagoya (JP); Miyoshi Makino, Nagoya (JP); Koichi Masuda, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 14/643,516

(22) Filed: Mar. 10, 2015

(65) Prior Publication Data

US 2015/0268187 A1 Sep. 24, 2015

(30) Foreign Application Priority Data

Mar. 19, 2014 (JP) ................................. 2014-055867

(51) Int. Cl.
*G01N 27/407* (2006.01)

(52) U.S. Cl.
CPC ....... *G01N 27/407* (2013.01); *G01N 27/4078* (2013.01)

(58) Field of Classification Search
CPC .............................. G01N 27/407–27/41; F01N 2560/00–2560/027
See application file for complete search history.

(56) References Cited

U.S. PATENT DOCUMENTS

| 5,759,365 A | 6/1998 | Yamada et al. |
| 2002/0003088 A1 | 1/2002 | Ozawa |
| 2003/0116435 A1* | 6/2003 | Satou ................. G01N 27/4077 204/424 |
| 2011/0094883 A1 | 4/2011 | Ito et al. |
| 2014/0102170 A1 | 4/2014 | Kato |

FOREIGN PATENT DOCUMENTS

| EP | 1167960 A1 | 1/2002 |
| EP | 2392920 A1 | 12/2011 |
| JP | 8-240558 A | 9/1996 |
| JP | 2005-156493 A | 6/2005 |
| JP | 4346424 B2 | 7/2009 |
| WO | 2013/005491 A1 | 1/2013 |

OTHER PUBLICATIONS

"Surface Texture From Ra to Rz," George Schuetz, Modern Machine Shop, Nov. 1, 2002, 2 pages, downloaded May 2, 2016 from http://www.mmsonline.com/columns/surface-texture-from-ra-to-rz.*
The Extended European Search Report for the corresponding European patent application No. 15159716.8 issued on Aug. 3, 2015.

* cited by examiner

*Primary Examiner* — Alexander Noguerola
(74) *Attorney, Agent, or Firm* — Global IP Counselors, LLP

(57) ABSTRACT

In a gas sensor 10, a powder compact 45a seals a void space between an inner peripheral surface 42c of metal-made main hardware 42 and a sensor element 20, and the inner peripheral surface 42c has arithmetic average roughness Ra of 0.5 to 5 μm. The gas sensor 10 includes supporters 44a and 44b, which are arranged in a penetration hole of the main hardware 42, which allow the sensor element 20 to penetrate therethrough, and which press the powder compact 45a in sandwiching relation from both sides in an axial direction. A surface of at least one of the supporters 44a and 44b has the arithmetic average roughness Ra of not more than 0.5 μm.

8 Claims, 6 Drawing Sheets

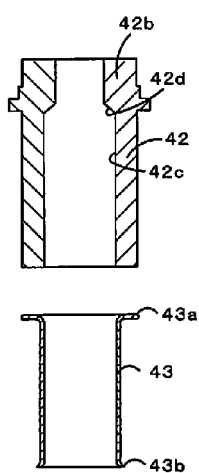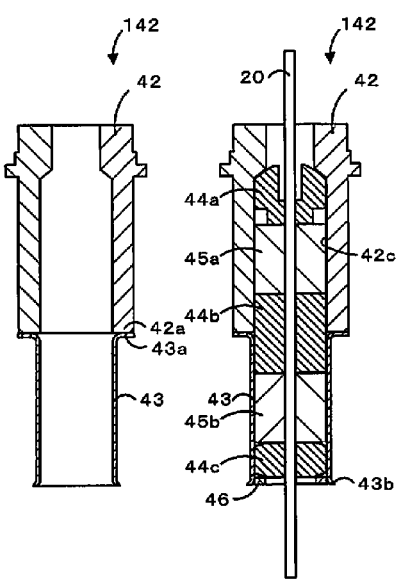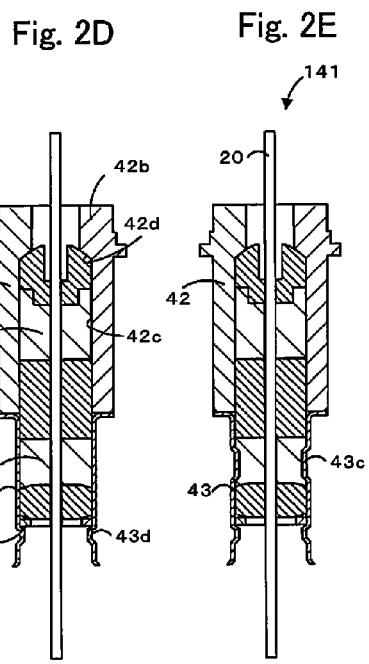

GAS SENSOR

BACKGROUND OF THE INVENTION

1. Field of the Invention

The present invention relates to a gas sensor.

2. Description of the Related Art

Hitherto, there is known a gas sensor for detecting a concentration of specific gas, such as NOx, which is contained in target gas of measurement, e.g., exhaust gas from an automobile. For example, Patent Literature (PTL) 1 discloses a gas sensor including a sensor element that detects a concentration of specific gas, a tubular member through which the sensor element penetrates, and a cover disposed at a free end of the sensor element and having a gas inlet through which the specific gas is introduced.

Furthermore, PTL 2 discloses a gas sensor including a ceramic holder (tubular member) having a recess and a penetration hole formed in a bottom portion of the recess, a gas sensor element inserted into both the recess and the penetration hole, and a sealing material (molten glass powder) filled into a void space between the gas sensor element and the recess. PTL 2 states that, in the disclosed gas sensor, a bonding failure between an inner peripheral surface of the recess of the ceramic holder and the sealing material can be suppressed and a good gas-tight state can be obtained by setting surface roughness of the inner peripheral surface of the recess of the ceramic holder to be not less than 0.3 µm, and by setting surface roughness of the bottom portion of the recess to be larger than that of the inner peripheral surface of the recess. PTL 2 further states that the surface roughness of the inner peripheral surface of the recess of the ceramic holder is preferably not less than 2 µm and more preferably not less than 5 µm.

CITATION LIST

Patent Literature

[PTL 1] International Publication No. 2013/005491
[PTL 2] Japanese Patent No. 4346424

SUMMARY OF INVENTION

In the relevant technical field, increasing gas tightness by sealing the void space between the sensor element and the tubular member with the sealing material as disclosed in PTL 2, for example, is important for the reason that higher gas tightness contributes to improving measurement accuracy of the gas sensor. On the other hand, further reduction in size of the gas sensor has been demanded in recent years. With the further reduction in size, however, an axial length of the filled sealing member becomes shorter, and the gas tightness is more apt to be insufficient. While the gas tightness can be enhanced by increasing a sealing pressure (sealing load) applied to the sealing material, an excessive increase of the sealing pressure may cause the problem, for example, that the sensor element or the tubular member is broken.

The present invention has been accomplished with intent to solve the above-mentioned problems, and a main object of the present invention is to further improve the gas tightness between the tubular member and the sensor element.

A gas sensor of the present invention includes:
a sensor element;
a tubular member made of metal and having a penetration hole through which the sensor element penetrates in an axial direction; and
a powder compact arranged in the penetration hole and filled between an inner peripheral surface of the penetration hole and the sensor element,
wherein at least a portion of the inner peripheral surface of the penetration hole of the tubular member, the portion being contacted with the powder compact, has arithmetic average roughness Ra of 0.5 to 5 µm.

In the gas sensor of the present invention, the powder compact seals a space between the inner peripheral surface of the metal-made tubular member and the sensor element, and at least a portion of the inner peripheral surface, the portion being contacted with the powder compact, has the arithmetic average roughness Ra of 0.5 to 5 µm. With that feature, gas tightness between the tubular member and the sensor element is relatively improved. The reason is presumably as follows. Since the arithmetic average roughness Ra of the inner peripheral surface of the tubular member is set to be not less than 0.5 µm, a contact area between the powder compact and the tubular member is increased, and an amount of gas leakage through a void space between the powder compact and the tubular member is reduced. Moreover, since the arithmetic average roughness Ra of the inner peripheral surface of the tubular member is set to be not more than 5 µm, it is possible to sufficiently fill the powder compact into valley portions (recesses) of the inner peripheral surface in comparison with the case where irregularities of the inner peripheral surface are excessively large, and to suppress degradation of the gas tightness, which may be caused by generation of the void space between the powder compact and the tubular member.

The gas sensor of the present invention may further include a first member and a second member, which press the powder compact in sandwiching relation from both sides in the axial direction, and a pressing surface of at least one of the first and second members, the pressing surface acting to press the powder compact, may have arithmetic average roughness Ra of not more than 0.5 µm. With that feature, the pressing surface becomes smoother than that in the case where the arithmetic average roughness Ra is set to be more than 0.5 µm, for example. Hence the powder compact is more easily spreadable in a direction along the pressing surface, i.e., in a radial direction of the tubular member. In other words, the powder compact is less apt to be caught by the pressing surface. As a result, a pressing force applied from at least one of the first and second members efficiently acts on the inner peripheral surface of the tubular member and the sensor element through the powder compact, and the gas tightness is further improved.

In the above-described gas sensor of the present invention, which includes the first and second members, the first and second members may be first and second supporters, which are arranged in the penetration hole, which allow the sensor element to penetrate therethrough, and which press the powder compact in sandwiching relation from both sides in the axial direction.

In that case, the tubular member may have a diameter contracted portion, and one of the first and second supporters may be arranged between the diameter contracted portion and the powder compact in the axial direction to press the powder compact by a pressing force applied from the diameter contracted portion. Alternatively, one of the first and second supporters may be arranged between the diameter contracted portion and the powder compact, and the other may be arranged between a bottom surface of the tubular member, the bottom surface being formed in the penetration hole, and the powder compact, such that the first and second supporters press the powder compact by being sandwiched between the diameter contracted portion and the bottom surface.

In the above-described gas sensor of the present invention, which includes the first and second members, one of the first and second members may be the tubular member, and the tubular member may have the inner peripheral surface and the pressing surface that has the arithmetic average roughness Ra of not more than 0.5 µm. In that case, the pressing surface of the tubular member may be a bottom surface of the tubular member, the bottom surface being formed in the penetration hole.

In the gas sensor of the present invention, an average particle diameter of particles constituting the powder compact may be 150 to 300 µm. With that feature, since the void space between the inner peripheral surface and the powder compact is further reduced, the gas tightness between the tubular member and the sensor element is further improved.

BRIEF DESCRIPTION OF THE DRAWINGS

FIG. 2A to 2E are sectional views schematically illustrating a manufacturing process of a primary assembly 141.

DESCRIPTION OF THE PREFERRED EMBODIMENTS

Figure 1:
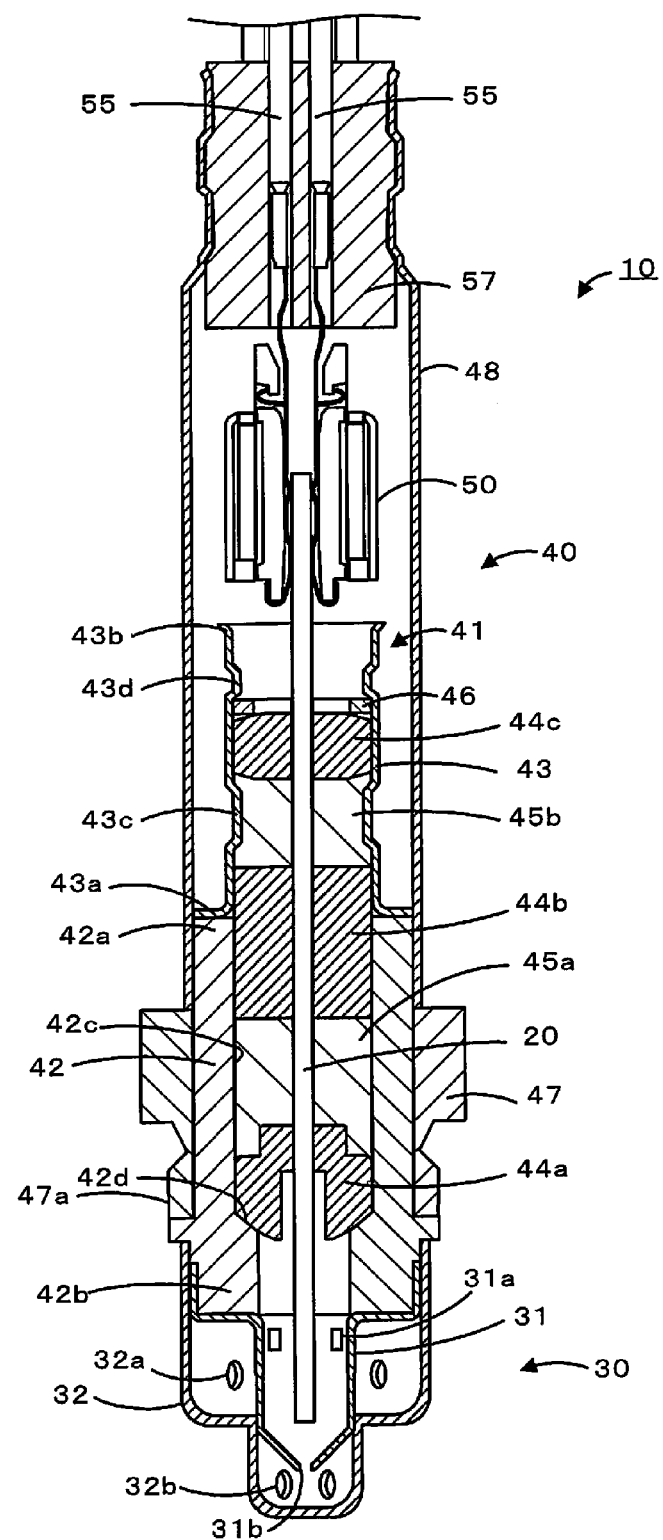
FIG. 1 is a vertical sectional view of a gas sensor 10.

An embodiment of the present invention will be described below with reference to the drawings. FIG. 1 is a vertical sectional view of a gas sensor 10 according to the embodiment of the present invention. As illustrated in FIG. 1, the gas sensor 10 includes a sensor element 20 that measures a specific gas component from target gas of measurement, a protective cover 30 that protects one end of the sensor element 20, and a sensor assembly 40 including a connector 50 that is electrically conducted to the sensor element 20. The gas sensor 10 is mounted to an exhaust gas pipe of a vehicle, for example, and is used to measure gas components, such as NOx and $O_2$, which are contained in exhaust gas, i.e., the target gas of measurement.

The sensor element 20 is an element in the form of a long slender plate, and is formed by stacking, e.g., six ceramic substrates each including an oxygen-ion conductive solid electrolyte layer made of zirconia ($ZrO_2$), for example. It is to be noted that an end (lower end in FIG. 1) of the sensor element 20 closer to the protective cover 30 is called a free end, and an end (upper end in FIG. 1) of the sensor element 20 closer to the connector 50 is called a base end. A base end surface and a rear surface of the sensor element 20 include electrodes (not illustrated) formed therein to apply a voltage to the sensor element 20 and to take out an electromotive force or a current, which is generated depending on the concentration of the gas component to be detected by the sensor element 20. Those electrodes are (though not illustrated) electrically conducted to electrodes formed at the free end of the sensor element 20 through electric paths inside the sensor element 20.

The protective cover 30 is disposed, as illustrated in FIG. 1, to surround the free end of the sensor element 20. The protective cover 30 includes an inner protective cover 31 that covers the free end of the sensor element 20, and an outer protective cover 32 that covers the inner protective cover 31. The inner protective cover 31 is formed in a tubular shape, and it has inner protective cover holes 31a and 31b allowing the target gas of measurement to pass therethrough. The outer protective cover 32 is formed in a tubular shape including a bottom, and it has outer protective cover holes 32a and 32b, in a side surface thereof, allowing the target gas of measurement to pass therethrough. The inner protective cover 31 and the outer protective cover 32 are each made of metal, e.g., stainless steel.

The sensor assembly 40 includes an element enclosing member 41 that encloses the sensor element 20 in a fixed state, a nut 47 mounted to the element enclosing member 41, an outer tube 48, and the connector 50 connected to the base end of the sensor element 20. The element enclosing member 41 serves to not only fix the sensor element 20, but also to seal a portion between a space defined within the protective cover 30 on the side closer to the free end of the sensor element and a space defined within the outer tube 48 on the side closer to the base end of the sensor element. The element enclosing member 41 includes tubular main hardware 42, a tubular inner tube 43 fixedly welded at its one end to the main hardware 42 in coaxial relation, supporters 44a to 44c enclosed in respective penetration holes within the main hardware 42 and the inner tube 43, power compacts 45a and 45b, and a metal ring 46.

The main hardware 42 is a metal-made member having an end portion 42a located at an upper end in FIG. 1, a thicker wall portion 42b located at a lower end, a penetration hole that penetrates through the main hardware 42 in an axial direction (up-and-down direction in FIG. 1), and an inner peripheral surface 42c of the penetration hole. The end portion 42a is welded to the inner tube 43. The thicker wall portion 42b has a bottom surface 42d that is a surface on the side closer to the base end (upper surface of the thicker wall portion 42b in FIG. 1), and that projects into the penetration hole, thus retaining the supporter 44a not to be jumped out downwards in FIG. 1. Spiral grooves (not illustrated) are formed in the inner peripheral surface 42c, and the inner peripheral surface 42c has arithmetic average roughness Ra of 0.5 to 5 µm with the presence of the spiral grooves. In addition, the inner peripheral surface 42c is contacted with the supporters 44a and 44b and the power compact 45a.

The inner tube 43 is a metal-made member having a thickness smaller than that of the main hardware 42, and it has a flange portion 43a at one end thereof on the side where the inner tube 43 is welded the main hardware 42, and a gradually expanding portion 43b that is positioned at the other end thereof on the side opposite to the flange portion 43a, and that has an inner diameter gradually increasing toward the other end. Furthermore, the inner tube 43 has a diameter contracted portion 43c that acts to press the powder compact 45b toward a center axis of the inner tube 43, and a diameter contracted portion 43d that acts to press the supporters 44a to 44c and the powder compacts 45a and 45b downwards in FIG. 1 through the metal ring 46. Portions of the inner tube 43 other than the flange portion 43a, the gradually expanding portion 43b, and the diameter contracted portions 43c and 43d have an inner diameter substantially the same as that of a portion of the main hardware 42 other than the thicker wall portion 42b (i.e., as an inner diameter of the inner peripheral surface 42c).

The supporters 44a to 44c are each a member made of ceramic, such as alumina, steatite, zirconia, or spinel. The powder compacts 45a and 45b are each obtained by molding powder of talc, alumina, boron nitride, or some other suitable ceramic. Surfaces of the supporters 44a to 44c preferably have arithmetic average roughness Ra of not more than 0.5 µm. An average diameter of particles constituting the powder compacts is preferably from 150 to 300 µm. The powder compact 45a is filled between the supporters 44a and 44b and is pressed in a state sandwiched from both sides (upper and lower sides) by the supporters 44a and 44b. The powder compact 45b is filled between the supporters 44b and 44c and is pressed in a state sandwiched from both sides (upper and lower sides) by the supporters 44b and 44c. Furthermore, the supporters 44a to 44c and the powder compacts 45a and 45b are entirely sandwiched between the diameter contracted portion 43d and the metal ring 46 on the upper side and the bottom surface 42d of the thicker wall portion 42b of the main hardware 42 on the lower side, and are pressed from above and below. The sensor element 20 is positioned to lie on respective center axes of the inner tube 43 and the main hardware 42, and to penetrate through the supporters 44a to 44c and the powder compacts 45a and 45b while the sensor element 20 is fixedly held by them.

The nut 47 is fixed coaxially with the main hardware 42, and it can be mounted to, e.g., the exhaust gas pipe of the vehicle through external threads 47a. The outer tube 48 covers respective peripheries of the inner tube 43, the sensor element 20, and the connector 50. Lead wires 55 connected to the connector 50 are led out to the outside from the outer tube 48. The lead wires 55 are electrically conducted to the electrodes of the sensor element 20 through the connector 50. Spaces between the outer tube 48 and the lead wires 55 are sealed by a rubber plug 57.

A method for manufacturing the gas sensor 10 will be described below. First, a primary assembly 141 made up of the element enclosing member 41 and the sensor element 20 is manufactured. FIG. 2A to 2E are sectional views schematically illustrating a manufacturing process of the primary assembly 141. The main hardware 42 and the inner tube 43 are initially prepared (FIG. 2A). The main hardware 42 and the inner tube 43 are manufactured by forging, for example. Furthermore, by inserting, e.g., a cutting tool into the penetration hole of the main hardware 42, spirals grooves are formed in the inner peripheral surface 42c of the main hardware 42 such that the inner peripheral surface 42c has the arithmetic average roughness Ra of 0.5 to 5 µm. Such spiral grooves are not necessarily required to be formed in an inner peripheral surface and the bottom surface 42d of the thicker wall portion 42b. At this stage, the flange portion 43a and the gradually expanding portion 43b are formed in the inner tube 43, but the diameter contracted portions 43c and 43d are not yet formed.

Then, the end portion 42a of the main hardware 42 and the flange portion 43a of the inner tube 43 are abutted with each other in coaxial relation by employing a jig (not illustrated). A composite body 142 is obtained by joining the main hardware 42 and the inner tube 43 with resistance welding (FIG. 2B). Thus, the main hardware 42 and the inner tube 43 are welded at contact surfaces of the end portion 42a and the flange portion 43a. Thereafter, the sensor element 20 is set to penetrate through the metal ring 46, the supporter 44c, the powder compact 45b, the supporter 44b, the powder compact 45a, and the supporter 44a in the mentioned order, and those components are inserted into the composite body 142 from the side including the gradually expanding portion 43b of the inner tube 43 (FIG. 2C). It is to be noted that bores are previously formed in the metal ring 46, the supporters 44a to 44c, and the powder compacts 45a and 45b along their center axes to allow the sensor element 20 to penetrate through those components. Here, because the inner tube 43 is flared at its end by the presence of the gradually expanding portion 43b, the above-mentioned components are easily inserted into the composite body 142. Moreover, because the arithmetic average roughness Ra of the inner peripheral surface 42c is not more than 5 µm, the supporters 44a and 44b and the powder compact 45a are less apt to contact or interfere with the inner peripheral surface 42c, and those components are easily inserted into the main hardware 42. The above-described insertion is performed by employing a jig such that the center axis of the inner tube 43 and the center axis of the sensor element 20 are aligned with each other on the basis of an outer diameter of the inner tube 43.

Then, the metal ring 46 and the main hardware 42 are pressed in a direction in which they approach each other, to compress the powder compacts 45a and 45b, thereby sealing the interiors of the main hardware 42 and the inner tube 43. In that state, a portion of the inner tube 43 at a position closer to the gradually expanding portion 43b than the metal ring 46 is crimped to form the diameter contracted portion 43d (FIG. 2D). As a result, a pressing force acting between the diameter contracted portion 43d and the metal ring 46 on one side and the bottom surface 42d of the main hardware 42 on the other side is maintained. In that state, the powder compact 45a is contacted with the inner peripheral surface 42c of the main hardware 42. Because the arithmetic average roughness Ra of the inner peripheral surface 42c is not less than 0.5 µm, a contact area between particles of the powder compact 45a and the inner peripheral surface 42c is increased. Furthermore, because the arithmetic average roughness Ra of the inner peripheral surface 42c is not more than 5 µm, the powder compact can be sufficiently filled into valley portions (recesses) of the inner peripheral surface 42c. In addition, while the powder compact 45a is pressed from above and below in the state sandwiched between the supporters 44a and 44b, the powder compact 45a is easily spreadable in a radial direction of the main hardware 42 because the arithmetic average roughness Ra of the surfaces of the supporters 44a and 44b is not more than 0.5 µm.

Then, a portion of the inner tube 43, the portion being located at a position corresponding to a lateral surface of the powder compact 45b, is crimped to form the diameter contracted portion 43c (FIG. 2E). As a result, the sealing against the interiors of the main hardware 42 and the inner tube 43 and the fixing of the sensor element 20 are ensured with higher reliability. The primary assembly 141 made up of the element enclosing member 41 and the sensor element 20 is thus obtained.

After manufacturing the primary assembly 141, the inner protective cover 31 and the outer protective cover 32 are fixedly welded to the main hardware 42 to form the protective cover 30, and the primary assembly 141 is inserted into the nut 47 such that the nut 47 is mounted to the main hardware 42. A secondary assembly is thus obtained. Moreover, the lead wires 55 extending through the rubber plug 57 and the connector 50 connected to the lead wires 55 are prepared. The connector 50 is connected to the base end side of the sensor element 20. Thereafter, the outer tube 48 is fixedly welded to the main hardware 42, whereby the gas sensor 10 illustrated in FIG. 1 is obtained.

Here, the correspondence relation between the components of this embodiment and components of the present invention is explained. The sensor element 20 in this embodiment corresponds to a sensor element in the present invention. The main hardware 42 and the inner tube 43 correspond to a tubular member. The inner peripheral surface 42c corresponds to an inner peripheral surface of a penetration hole. The powder compact 45a corresponds to a powder compact. The supporters 44a and 44b correspond to first and second members, respectively. The supporters 44a and 44b further correspond to first and second supporters, respectively. The diameter contracted portions 43c and 43d correspond to a diameter contracted portion.

In the above-described gas sensor 10 according to this embodiment, the powder compact 45a seals a void space between the inner peripheral surface 42c of the metal-made main hardware 42 and the sensor element 20, and the inner peripheral surface 42c has the arithmetic average roughness Ra of 0.5 to 5 µm. With that feature, the gas tightness between the main hardware 42 and the sensor element 20 is relatively improved. The reason is presumably as follows. Since the arithmetic average roughness Ra of the inner peripheral surface 42c of the main hardware 42 is set to be not less than 0.5 µm, a contact area between the powder compact 45a and the main hardware 42 is increased, and an amount of gas leakage through the void space between the powder compact 45a and the main hardware 42 (specifically, the inner peripheral surface 42c) is reduced. Moreover, since the arithmetic average roughness Ra of the inner peripheral surface 42c is set to be not more than 5 µm, it is possible to sufficiently fill the powder compact 45a into the valley portions (recesses) of the inner peripheral surface 42c in comparison with the case where irregularities of the inner peripheral surface 42c are excessively large, and to suppress degradation of the gas tightness, which may be caused by generation of the void space between the powder compact 45a and the main hardware 42 (specifically, the inner peripheral surface 42c).

Furthermore, the gas sensor 10 includes the supporters 44a and 44b, which are arranged in the penetration hole of the main hardware 42, which allow the sensor element 20 to penetrate therethrough, and which act to press the powder compact 45a from both sides in the axial direction in a sandwiching state. The arithmetic average roughness Ra of at least one of the surfaces of the supporters 44a and 44b is set to be not more than 0.5 µm. Therefore, the supporters 44a and 44b have smoother pressing surfaces than those in the case where the arithmetic average roughness Ra is set to be more than 0.5 µm, for example. Hence the powder compact 45a is more easily spreadable in a direction along the pressing surfaces, i.e., in the radial direction of the main hardware 42. In other words, the powder compact 45a is less apt to be caught by the pressing surfaces. As a result, pressing forces applied from the supporters 44a and 44b efficiently act on the inner peripheral surface 42c of the main hardware 42 and the sensor element 20 through the powder compact 45a, and the gas tightness is further improved. In addition, the powder compact 45b is pressed from both sides in the axial direction in the state sandwiched between the supporters 44b and 44c. Accordingly, when at least one of the surfaces of the supporters 44b and 44c has the arithmetic average roughness Ra of not more than 0.5 µm, pressing forces applied from the supporters 44b and 44c efficiently act on an inner peripheral surface of the inner tube 43 and the sensor element 20 through the powder compact 45b, and the gas tightness is further improved.

Moreover, since the average diameter of the particles constituting the powder compact 45a is set to 150 to 300 µm, the void space generated between the inner peripheral surface 42c and the powder compact 45a is further reduced. As a result, the gas tightness between the main hardware 42 and the sensor element 20 is further improved.

It is apparent that the present invention is not limited to the above-described embodiment at all and various embodiments can be made within the technical scope of the present invention.

Figure 3:
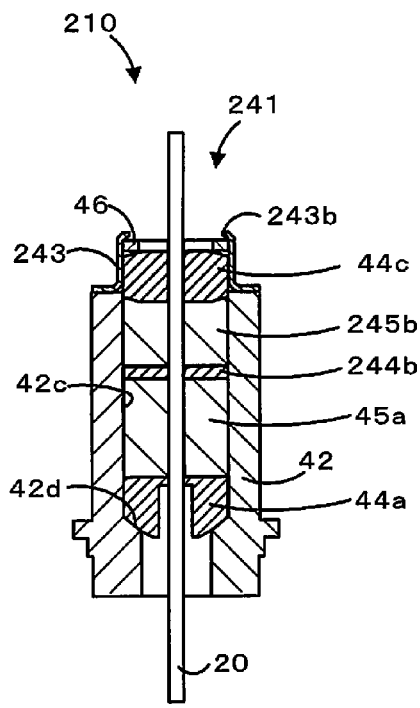
FIG. 3 is a vertical sectional view of a gas sensor 210 according to a modification.

For example, while the inner tube 43 has the diameter contracted portion 43c in the above-described embodiment, the diameter contracted portion 43c may be omitted. Furthermore, the size of the inner tube 43 in the axial direction may be shorter than that in FIG. 1. FIG. 3 is a vertical sectional view of a gas sensor 210 according to a modification in such a case. FIG. 3 illustrates only an element enclosing member 241 and the sensor element 20 among components of the gas sensor 210. In the element enclosing member 241, as illustrated in FIG. 3, a length of an inner tube 243 in the axial direction is shorter than that of the inner tube 43 in FIG. 1. Moreover, the diameter contracted portions 43c and 43d and the gradually expanding portion 43b are not formed in the inner tube 243. Instead, an opening end at the base end side (upper end in FIG. 3) of the inner tube 243 is bent to form a diameter contracted portion 243b. The supporter 44a, the powder compact 45a, a supporter 244b, a powder compact 245b, the supporter 44c, and the metal ring 46 are successively arranged in the mentioned order between the bottom surface 42d of the main hardware 42 and the diameter contracted portion 243b. The supporter 244b and the powder compact 245b have shorter lengths in the axial direction than the supporter 44b and the powder compact 45b illustrated in FIG. 1, respectively. Similar advantageous effects to those in the above-described embodiment are also obtained with the gas sensor 210. For example, by setting the arithmetic average roughness Ra of the inner peripheral surface 42c to be 0.5 to 5 µm, the gas tightness between the main hardware 42 and the sensor element 20 is relatively improved. When the length of the element enclosing member 241 in the axial direction is shortened, for example, by shortening the length of the inner tube 43 in the axial direction, the gas tightness tends to reduce. However, since the gas tightness is improved by setting the arithmetic average roughness Ra of the inner peripheral surface 42c to be 0.5 to 5 µm, the eventual gas tightness can be avoided from being reduced as a result of the above-mentioned improvement in the gas tightness. Stated in another way, even when a length of the gas sensor in the axial direction is shortened in comparison with that of a gas sensor in which the arithmetic average roughness Ra of the inner peripheral surface 42c is not in the range of 0.5 to 5 µm, the gas tightness can be held at the same level. Thus, the size of the gas sensor 210 can be reduced. While, in the gas sensor 210 of FIG. 3, the length of the inner tube 243 in the axial direction is shorter than that of the inner tube 43 in FIG. 1, the length of the main hardware 42 in the axial direction may be shortened instead.

Figure 4:
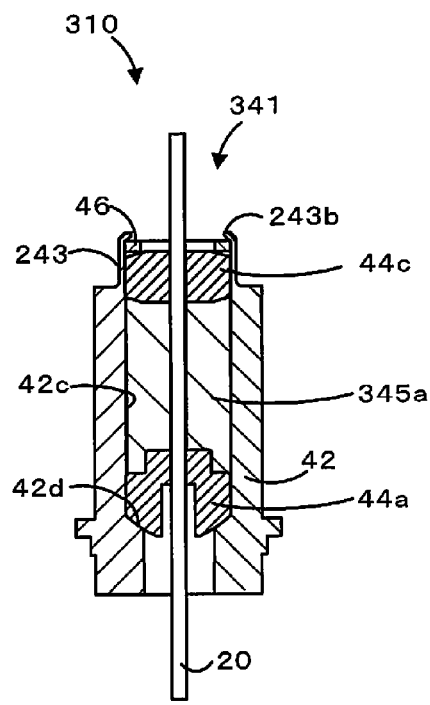
FIG. 4 is a vertical sectional view of a gas sensor 310 according to another modification.

In the gas sensor 210 of FIG. 3, the supporter 244b may be dispensed with. FIG. 4 is a vertical sectional view of a gas sensor 310 according to another modification in such a case. In an element enclosing member 341 of the gas sensor 310, a powder compact 345a is pressed from above and below in a state sandwiched between the supporter 44a and the supporter 44c. Similar advantageous effects to those in the above-described embodiment are also obtained with the gas sensor 310. It is to be noted that, in FIG. 4, the main hardware 42 and the inner tube 243 are formed integrally with each other, as seen from the drawing.

While, in the above-described embodiment, the arithmetic average roughness Ra is set to 0.5 to 5 μm over the entire inner peripheral surface 42c of the main hardware 42, the arithmetic average roughness Ra is just required to be 0.5 to 5 μm at least in a region where the inner peripheral surface 42c is contacted with the powder compact 45a.

In the above-described embodiment, the inner peripheral surface of the inner tube 43 may be formed to have the arithmetic average roughness Ra of 0.5 to 5 μm. With that feature, the void space generated between the powder compact 45b and the inner peripheral surface of the inner tube 43 is reduced, whereby the gas tightness between the inner tube 43 and the sensor element 20 is further improved.

In the above-described embodiment, when, among the surfaces of the supporter 44a, at least the surface (upper surface in FIG. 1) pressing the powder compact 45a has the arithmetic average roughness Ra of not more than 0.5 μm, the advantageous effect of making the powder compact 45a more easily spreadable in the radial direction is obtained as in the above-described embodiment. That point is similarly applied to the supporter 44b.

In the above-described embodiment, the surface of the sensor element 20 may be formed to have the arithmetic average roughness Ra of 0.5 to 5 μm. With that feature, because the arithmetic average roughness Ra is not less than 0.5 μm, a contact area between each of the powder compacts 45a and 45b and the sensor element 20 is increased, and because the arithmetic average roughness Ra is not more than 5 μm, the powder compacts 45a and 45b can be sufficiently filled into valley portions (recesses) of the surface of the sensor element 20. Therefore, the gas tightness between each of the main hardware 42 and the inner tube 43 and the sensor element 20 is further improved.

While, in the above-described embodiment, the spiral grooves are formed in the inner peripheral surface 42c by the cutting tool, suitable one of other machining methods may also be used on condition that the method can form the inner peripheral surface 42c with the arithmetic average roughness Ra of 0.5 to 5 μm. For example, grooves having some other suitable shape than the spiral shape may be formed in the inner peripheral surface 42c. As an alternative, the arithmetic average roughness Ra of the inner peripheral surface 42c may be set to 0.5 to 5 μm by roughing the inner peripheral surface 42c with sand blasting.

Figure 5:
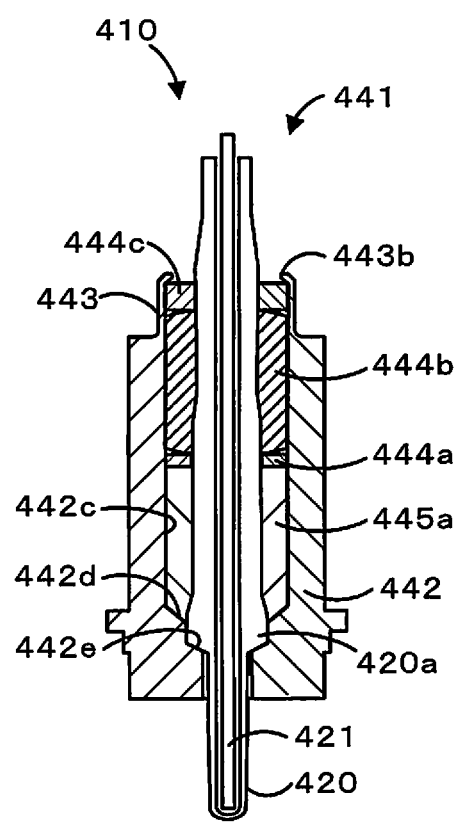
FIG. 5 is a vertical sectional view of a gas sensor 410 according to still another modification.

While, in the above-described embodiment, the sensor element 20 is an element in the form a plate, the shape of the sensor element 20 is not limited to the plate-like form. For example, the sensor element 20 may have a tubular shape. A gas sensor including a tubular sensor element is disclosed in, e.g., Japanese Unexamined Patent Application Publication No. 8-240558. FIG. 5 is a vertical sectional view of a gas sensor 410 according to still another modification in such a case. FIG. 5 illustrates only an element enclosing member 441 and a sensor element 420 among components of the gas sensor 410. The gas sensor 410 includes the sensor element 420 and the element enclosing member 441. The sensor element 420 is formed substantially in a cylindrical shape including a bottom and being opened at one end in a lengthwise direction (i.e., at an upper end in FIG. 5). A heater 421 is inserted into a central space of the sensor element 420. The element enclosing member 441 includes tubular main hardware 442, and a tubular inner tube 443 formed coaxially with the main hardware 442. The element enclosing member 441 further includes a packing 444a, a supporter 444b, a packing 444c, and a powder compact 445a, which are enclosed in penetration holes formed inside the main hardware 442 and the inner tube 443. The main hardware 442 has an inner peripheral surface 442c that defines the penetration hole formed therein. The main hardware 442 has a similar shape to that of the main hardware 42 in FIG. 4 except for that two bottom surfaces 442d and 442e are formed to define the penetration hole of the main hardware 442. The bottom surface 442d is formed at a position closer to an outer periphery of the main hardware 442 (namely, farther away from a center axis of the sensor element 420) than the bottom surface 442e, and it is contacted with the powder compact 445a. The bottom surface 442e is contacted with a gradually expanding portion 420a of the sensor element 420, namely with a portion of the sensor element 420, which has a larger diameter than a lower portion thereof in FIG. 5. In a state contacting with the gradually expanding portion 420a, the bottom surface 442e retains the sensor element 420 not to be jumped out downwards in FIG. 5. The inner tube 443 has a similar shape to that of the inner tube 243 in FIG. 4, and a diameter contracted portion 443b is formed at an end (upper end in FIG. 5) of the inner tube 443. The main hardware 442 and the inner tube 443 are formed integrally with each other. Each packing 444a or 444c is formed, for example, by an elastic body made of, e.g., resin. The supporter 444b is a member made of ceramic similarly to the supporters 44a and 44c in FIG. 4. The powder compact 445a is filled in a space surrounded by the inner peripheral surface 442c, the bottom surface 442d, an outer peripheral surface of the sensor element 420, and a lower surface of the packing 444a. The powder compact 445a, the packing 444a, the supporter 444b, and the packing 444c are pressed from both sides (from above and below in FIG. 5) in the axial direction in a state sandwiched between the bottom surface 442d and the diameter contracted portion 443b. Such an arrangement generates a pressing force that acts to press the powder compact 445a in the state sandwiched between the bottom surface 442d and the lower surface of the packing 444a, thereby sealing the interior of the main hardware 442. Similar advantageous effects to those in the above-described embodiment are also obtained with the gas sensor 410. For example, by setting the arithmetic average roughness Ra of the inner peripheral surface 442c to be 0.5 to 5 μm, the gas tightness between the main hardware 442 and the sensor element 420 is relatively improved. In addition, the gas tightness is further improved by setting the arithmetic average roughness Ra of at least one of the bottom surface 442d, which serves as the pressing surface to press the powder compact 445a, and the lower surface of the packing 444a, which serves also as the pressing surface, to be not more than 0.5 μm.

In the gas sensor 410 according to the modification illustrated in FIG. 5, as described above, the bottom surface 442d of the main hardware 442 is directly contacted with the powder compact 445a such that the bottom surface 442d serves as the pressing surface. The gas sensor 10 according to the above embodiment and the gas sensors 210 and 310 illustrated in FIGS. 3 and 4 may also be constituted, for example, such that the supporter 44a is omitted and the bottom surface 42d of the main hardware 42 serves as the pressing surface to directly press the powder compact 45a (or the powder compact 345a in FIG. 4). In such a case, as in the gas sensor 410 of FIG. 5, the gas tightness is further improved by setting the arithmetic average roughness Ra of the bottom surface 42d to be not more than 0.5 µm. Conversely, in the gas sensor 410 of FIG. 5, the supporter 44a may be arranged between the bottom surface 442d of the main hardware 442 and the powder compact 445a as in the gas sensor 10 according to the above embodiment and the gas sensors 210 and 310 illustrated in FIGS. 3 and 4. Thus, two members (first and second members) for pressing the powder compact in sandwiching relation from both sides in the axial direction of the sensor element may be any type of members. When, in at least one of the first and second members, the pressing surface acting to press the powder compact has the arithmetic average roughness Ra of not more than 0.5 µm, the advantageous effect of making the powder compact more easily spreadable in the direction along the pressing surface and further improving the gas tightness is obtained as in the above-described embodiment.

As described above in the embodiment, the gas tightness between the main hardware 42 and the sensor element 20 is relatively improved by setting the arithmetic average roughness Ra of the inner peripheral surface 42c to be 0.5 to 5 µm, and the gas tightness is further improved by setting the average diameter of the particles constituting the powder compact 45a to be 150 to 300 µm. This means that a ratio=(average diameter of the particles constituting the powder compact 45a)/(arithmetic average roughness Ra of the inner peripheral surface 42c) may be set to 30 to 600. When the ratio falls within such a numerical range, the gas tightness between the main hardware 42 and the sensor element 20 is further improved as in the above-described embodiment.

EXAMPLES

Experimental Examples 1 to 7

Experimental Examples 1 to 7 were each obtained, as a part of the gas sensor, by fabricating the primary assembly made up of the element enclosing member 341 and the sensor element 20 illustrated in FIG. 4, and by mounting the protective cover 30 and the nut 47, including the external threads 47a, to the primary assembly, thus fabricating the secondary assembly in the same manner as the above-described manufacturing method. Experimental Examples 1 to 7 had the same configuration except that the arithmetic average roughness Ra of the inner peripheral surface 42c was different among them. More specifically, the main hardware 42 and the inner tube 243 were made of stainless steel and formed by forging. The inner peripheral surface 42c of the main hardware 42 had the inner diameter of 9 mm and the axial length of 20.7 mm. The thicker wall portion 42b had the inner diameter of 5.9 mm and the axial length of 6.4 mm. The axial length of the inner tube 43 was 4.3 mm, and the inner diameter of the diameter contracted portion 243b was 9 mm. The supporters 44a and 44c were each a ceramic sintered body made of alumina. The axial length of the supporter 44a was 7.6 mm, and the axial length of the supporter 44c was 4.5 mm. For the surfaces of the supporters 44a and 44c, the arithmetic average roughness Ra was set to 0.45 µm in the supporter 44a and 0.3 µm in the supporter 44c. The powder compact 345a was prepared by molding talc powder with an average particle diameter of 244 µm. An amount (2.2 g) of the talc powder was adjusted such that the sealing load applied to the powder compact 345a from above and below in the main hardware 42 was 800 kgf. Respective values of the arithmetic average roughness Ra of the inner peripheral surface 42c in Experimental Examples 1 to 7 were 0.06 µm, 0.50 µm, 0.76 µm, 2.00 µm, 3.00 µm, 5.00 µm, and 10.00 µm. In Experimental Example 1, the cutting process to form the spiral grooves in the inner peripheral surface 42c was not performed.

Experimental Examples 8 to 28

Experimental Examples 8 to 14 were obtained by fabricating similar secondary assemblies to those in Experimental Examples 1 to 7 except that the sealing load applied to the powder compact 345a was changed to 1000 kgf. Experimental Examples 15 to 21 were obtained by fabricating similar secondary assemblies to those in Experimental Examples 1 to 7 except that the sealing load applied to the powder compact 345a was changed to 1400 kgf. Experimental Examples 22 to 28 were obtained by fabricating similar secondary assemblies to those in Experimental Examples 1 to 7 except that the sealing load applied to the powder compact 345a was changed to 2000 kgf. The amount of talc powder used in each of those Experimental Examples was 2.2 g.

[Evaluation Tests]

Figure 6:
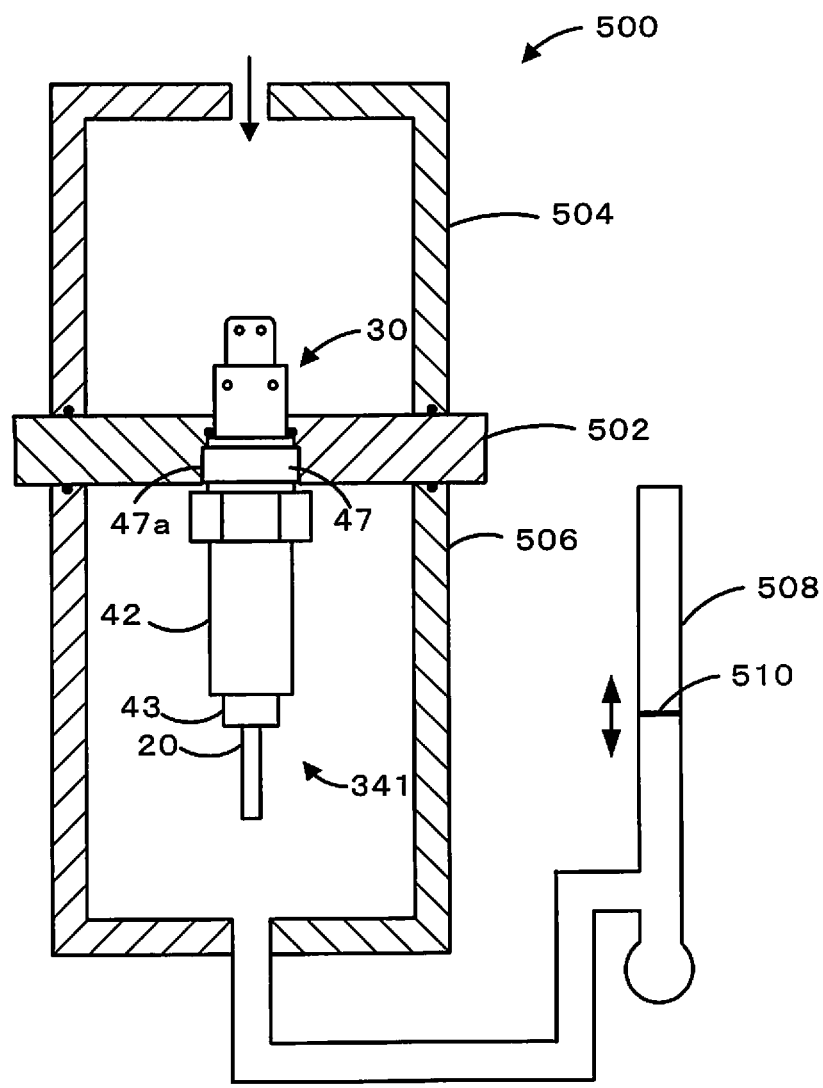
FIG. 6 is an illustration to explain a gas tightness test using a test apparatus 500.

The gas tightness effectuated by the powder compact 345a between each of the main hardware 42 and the inner tube 43 and the sensor element 20 was tested for the secondary assemblies of Experimental Examples 1 to 28. FIG. 6 is an illustration to explain a gas tightness test using a test apparatus 500. As illustrated in FIG. 6, the test apparatus 500 includes a mounting jig 502 having internal threads to which the external threads 47a in the secondary assembly can be fitted, an upper cover 504 and a lower cover 506 that cover respectively the upper side and the lower side of the mounting jig 502, and a pipe 508 that is connected to an opening of the lower cover 506, and that extends with its axial direction set in a vertical direction. Joint portions between adjacent two of the upper cover 504, the mounting jig 502, and the lower cover 506 are sealed by O-rings. After wrapping a sealing tape over the external threads 47a, the secondary assembly was mounted to the internal threads of the mounting jig 502 of the test apparatus 500, and was fixed by employing a torque wrench (4.5 Nm). Inner spaces of the upper cover 504 and the lower cover 506 were thus brought into a state where gas is allowed to flow between the inner spaces only through the interior of the secondary assembly (i.e., the interiors of the main hardware 42 and the inner tube 43). Then, a film 510 made of soap water was formed to stretch over an inner space of the pipe 508. In that state, air was supplied through an upper opening in the upper cover 504 to apply a pressure of 0.4 MPaG for one minute, and an amount (mm) of rise of the film 510 was measured by employing a scale. The rise amount was converted to a leakage amount (cc/min). It is to be noted that the amount of rise of 1 mm corresponds to the leakage amount of 0.01 cc (=0.01 cm$^3$). A smaller value of the leakage amount means that the gas tightness between each of the main hardware 42 and the inner tube 43 and the sensor element 20 is higher.

Figure 7:
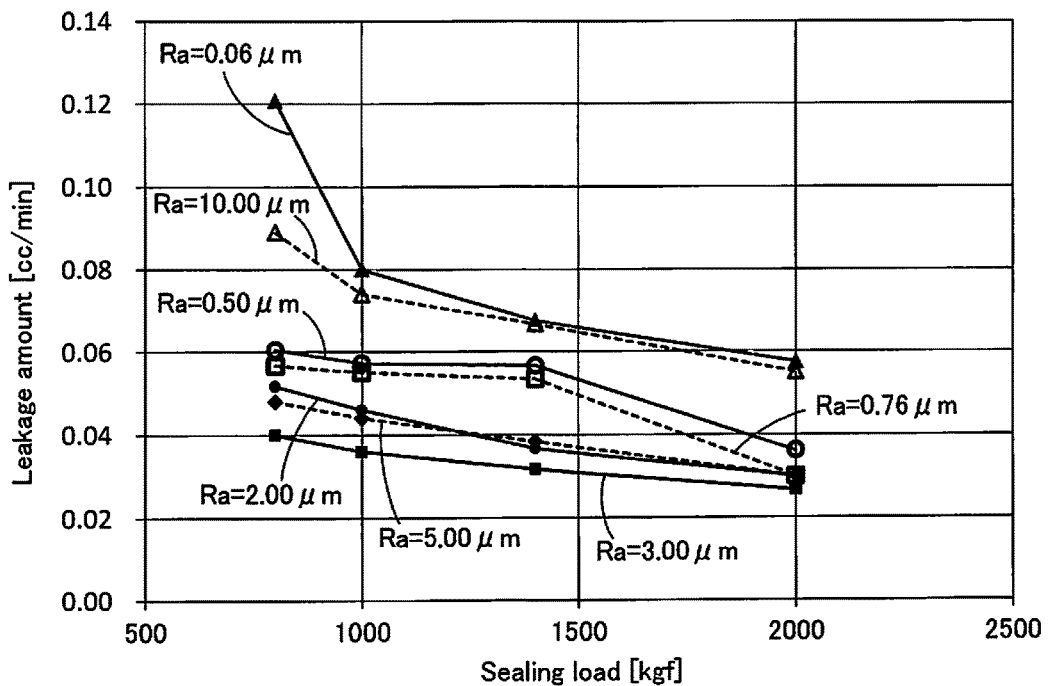
FIG. 7 is a graph representing a relation between a sealing load and a leakage amount in Experimental Examples 1 to 28.
Figure 8:
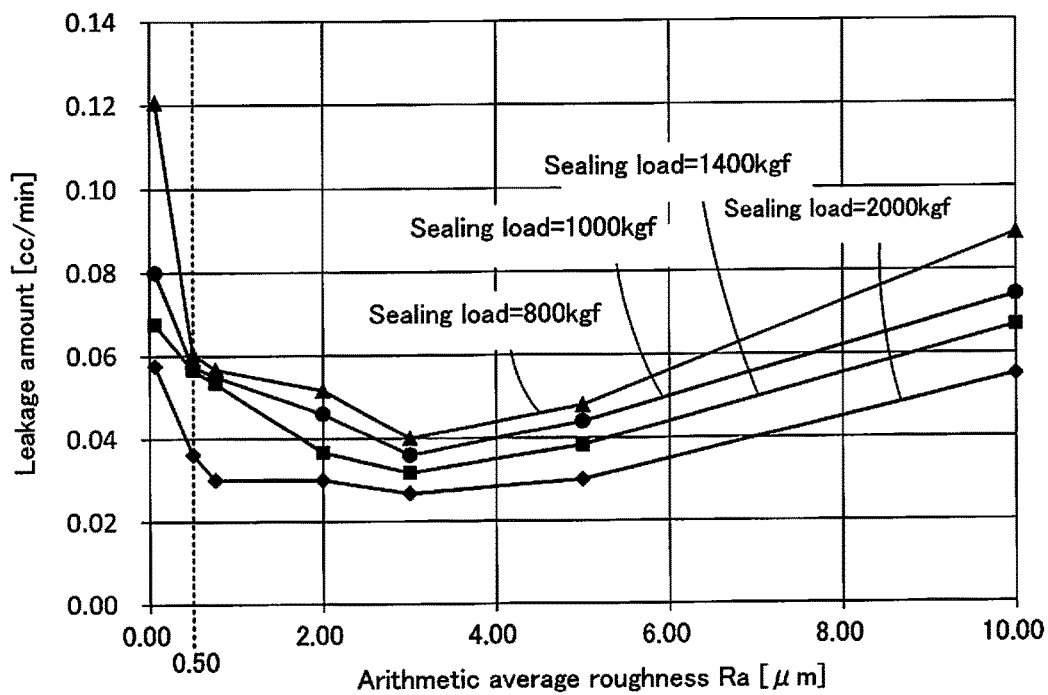
FIG. 8 is a graph representing a relation between arithmetic average roughness Ra and a leakage amount in Experimental Examples 1 to 28.

Table 1 lists the sealing load (kgf) applied to the powder compact 345a, the arithmetic average roughness Ra (µm) of the inner peripheral surface 42c, and the measured leakage amount (cc/min) for each of Experimental Examples 1 to 28. The leakage amount in Table 1 is indicated by an average of values measured on three samples for each Experimental Example FIG. 7 is a graph representing a relation between the sealing load and the leakage amount in Experimental Examples 1 to 28. FIG. 8 is a graph representing a relation between the arithmetic average roughness Ra of the inner peripheral surface 42c and the leakage amount in Experimental Examples 1 to 28.

TABLE 1

|  | Sealing load (kgf) | Arithmetic average roughness Ra (μm) | Leakage amount (cc/min) |
| --- | --- | --- | --- |
| Experimental Example 1 | 800 | 0.06 | 0.1206 |
| Experimental Example 2 | 800 | 0.50 | 0.0605 |
| Experimental Example 3 | 800 | 0.76 | 0.0567 |
| Experimental Example 4 | 800 | 2.00 | 0.0517 |
| Experimental Example 5 | 800 | 3.00 | 0.0400 |
| Experimental Example 6 | 800 | 5.00 | 0.0480 |
| Experimental Example 7 | 800 | 10.00 | 0.0590 |
| Experimental Example 8 | 1000 | 0.06 | 0.0800 |
| Experimental Example 9 | 1000 | 0.50 | 0.0573 |
| Experimental Example 10 | 1000 | 0.76 | 0.0550 |
| Experimental Example 11 | 1000 | 2.00 | 0.0460 |
| Experimental Example 12 | 1000 | 3.00 | 0.0360 |
| Experimental Example 13 | 1000 | 5.00 | 0.0440 |
| Experimental Example 14 | 1000 | 10.00 | 0.0540 |
| Experimental Example 15 | 1400 | 0.06 | 0.0675 |
| Experimental Example 16 | 1400 | 0.50 | 0.0566 |
| Experimental Example 17 | 1400 | 0.76 | 0.0533 |
| Experimental Example 18 | 1400 | 2.00 | 0.0367 |
| Experimental Example 19 | 1400 | 3.00 | 0.0317 |
| Experimental Example 20 | 1400 | 5.00 | 0.0383 |
| Experimental Example 21 | 1400 | 10.00 | 0.0467 |
| Experimental Example 22 | 2000 | 0.06 | 0.0575 |
| Experimental Example 23 | 2000 | 0.50 | 0.0361 |
| Experimental Example 24 | 2000 | 0.76 | 0.0300 |
| Experimental Example 25 | 2000 | 2.00 | 0.0300 |
| Experimental Example 26 | 2000 | 3.00 | 0.0267 |
| Experimental Example 27 | 2000 | 5.00 | 0.0300 |
| Experimental Example 28 | 2000 | 10.00 | 0.0350 |

As seen from Table 1 and FIGS. 7 and 8, comparing Experimental Examples where the same sealing load was applied, the leakage amount was smaller in Experimental Examples where the arithmetic average roughness Ra of the inner peripheral surface 42c was in the range of 0.5 to 5 μm than in Experimental Examples where it was not in that range. Furthermore, as seen from FIG. 7, for example, when the sealing load was gradually reduced, the leakage amount was less apt to increase in Experimental Examples where the arithmetic average roughness Ra of the inner peripheral surface 42c was in the range of 0.5 to 5 μm. In other words, the leakage amount was held small even at the lower sealing load in those Experimental Examples.

Among Experimental Examples 1 to 28, Experimental Examples 2 to 6, 9 to 13, 16 to 20, and 23 to 27 correspond to Examples implementing the present invention, and the remaining Experimental Examples correspond to Comparative Examples. However, the present invention is not limited to the above-described embodiment.

The present application claims priority of Japanese Patent Application No. 2014-055867 filed on Mar. 19, 2014, the entire contents of which are incorporated herein by reference.

What is claimed is:

1. A gas sensor comprising:
a sensor element;
a tubular member made of metal and having a penetration hole through which the sensor element penetrates in an axial direction;
a powder compact arranged in the penetration hole and filled between an inner peripheral surface of the penetration hole and the sensor element; and
a first member and a second member which press the powder compact in sandwiching relation from both sides in the axial direction,
at least a portion of the inner peripheral surface of the penetration hole of the tubular member, the portion being contacted with the powder compact, having an arithmetic average roughness Ra of 0.5 to 5 μm, and
a pressing surface of at least one of the first and second members, the pressing surface acting to press the powder compact, having an arithmetic average roughness Ra of not more than 0.5 μm.

2. The gas sensor according to claim 1, wherein the first and second members are first and second supporters, which are arranged in the penetration hole, which allow the sensor element to penetrate therethrough, and which press the powder compact in sandwiching relation from both sides in the axial direction.

3. The gas sensor according to claim 2, wherein the tubular member has a diameter contracted portion, and
one of the first and second supporters is arranged between the diameter contracted portion and the powder compact in the axial direction to press the powder compact by a pressing force applied from the diameter contracted portion.

4. The gas sensor according to claim 3, wherein one of the first and second supporters is arranged between the diameter contracted portion and the powder compact, and the other is arranged between a bottom surface of the tubular member, the bottom surface being formed in the penetration hole, and the powder compact, such that the first and second supporters press the powder compact by being sandwiched between the diameter contracted portion and the bottom surface.

5. The gas sensor according to claim 2, wherein an average particle diameter of particles constituting the powder compact is 150 to 300 μm.

6. The gas sensor according to claim 1, wherein one of the first and second members is the tubular member, and
the tubular member has the inner peripheral surface and the pressing surface that has the arithmetic average roughness Ra of not more than 0.5 μm.

7. The gas sensor according to claim 1, wherein an average particle diameter of particles constituting the powder compact is 150 to 300 μm.

8. The gas sensor according to claim 1, wherein the powder compact is in contact with both the inner peripheral surface of the penetration hole and the sensor element.

* * * * *